United States Patent
Rydell

[11] Patent Number: 6,079,868
[45] Date of Patent: Jun. 27, 2000

[54] STATIC MIXER

[75] Inventor: Mark A. Rydell, Golden Valley, Minn.

[73] Assignee: Advanced Bio Surfaces, Inc., Minnetonka, Minn.

[21] Appl. No.: 09/033,261

[22] Filed: Mar. 2, 1998

Related U.S. Application Data

[63] Continuation-in-part of application No. 08/993,468, Dec. 18, 1997.

[51] Int. Cl.[7] .............................. B01F 15/02; B67D 5/60; A61M 31/00; A61M 5/31
[52] U.S. Cl. .......................... 366/189; 366/192; 604/416; 604/61; 222/145.6; 222/325
[58] Field of Search .............................. 366/154.1, 158.5, 366/162.1, 162.3, 176.1, 176.3, 174.1, 177.1, 181.5, 182.2, 189, 190, 192, 339, 336; 222/136, 137, 142, 145.5, 145.6, 325; 604/416, 61, 62

[56] References Cited

U.S. PATENT DOCUMENTS

| | | |
|---|---|---|
| D. 394,994 | 6/1998 | Dreve . |
| 1,087,572 | 2/1914 | Craven . |
| 3,223,083 | 12/1965 | Cobey . |
| 3,286,992 | 11/1966 | Armeniades et al. . |
| 3,309,814 | 3/1967 | Langley . |
| 3,635,444 | 1/1972 | Potter . |
| 3,664,638 | 5/1972 | Grout et al. . |
| 3,774,809 | 11/1973 | Bratton . |
| 3,806,097 | 4/1974 | Devellian et al. . |
| 3,861,567 | 1/1975 | Davis, Jr. . |
| 3,923,288 | 12/1975 | King . |
| 3,984,033 | 10/1976 | Groth et al. . |
| 4,014,463 | 3/1977 | Hermann . |
| 4,040,420 | 8/1977 | Speer . |
| 4,041,463 | 8/1977 | Slutzky et al. . |
| 4,044,758 | 8/1977 | Patel . |
| 4,050,676 | 9/1977 | Morishima et al. . |
| 4,183,682 | 1/1980 | Lieffers . |
| 4,338,925 | 7/1982 | Miller . |
| 4,359,049 | 11/1982 | Redl et al. . |
| 4,538,920 | 9/1985 | Drake ....................................... 366/177 |
| 4,583,934 | 4/1986 | Hata et al. . |
| 4,631,055 | 12/1986 | Redl et al. . |
| 4,643,336 | 2/1987 | Mandeville et al. ..................... 366/339 |
| 4,671,263 | 6/1987 | Draenert . |
| 4,676,657 | 6/1987 | Botrie ...................................... 366/177 |
| 4,735,616 | 4/1988 | Eibl . |
| 4,767,026 | 8/1988 | Keller et al. ............................. 366/339 |
| 4,846,373 | 7/1989 | Penn et al. ............................... 222/137 |
| 4,934,827 | 6/1990 | Taschke et al. .......................... 366/162 |
| 4,995,540 | 2/1991 | Colin et al. .............................. 222/132 |
| 5,071,040 | 12/1991 | Laptewicz, Jr. ......................... 366/196 |
| 5,104,005 | 4/1992 | Schneider, Jr. et al. ................. 272/137 |
| 5,203,476 | 4/1993 | Keller . |
| 5,207,357 | 5/1993 | Aronie et al. . |
| 5,263,614 | 11/1993 | Jacobsen et al. . |
| 5,464,128 | 11/1995 | Keller . |
| 5,474,540 | 12/1995 | Miller et al. . |
| 5,556,429 | 9/1996 | Felt . |
| 5,566,860 | 10/1996 | Schiltz et al. . |
| 5,664,701 | 9/1997 | Massena . |
| 5,853,774 | 12/1998 | Dreve . |
| 5,860,739 | 1/1999 | Cannon ................................... 366/189 |
| 5,909,959 | 6/1999 | Gerich ..................................... 366/339 |

FOREIGN PATENT DOCUMENTS

WO9726847 7/1977 WIPO .

Primary Examiner—Tony G. Soohoo
Attorney, Agent, or Firm—Fredrikson & Byron, PA

[57] ABSTRACT

A device for mixing and delivering a curable biomaterial using minimally invasive techniques. The device provides a mixing path that is configured to contribute a longitudinal distance dimension to the device that is considerably less than the length of the mixing path itself. In so doing, the device can provide improved ergonomic control and single-handed operation in the course of mixing biomaterial components, in order to initiate cure, and delivering the mixed biomaterial through a delivery conduit and to a tissue site in vivo. Optional features of the device include the ability to warm the biomaterial components, to position or retract a protective sheath covering the delivery conduit, and the ability to divert or shunt an initial volume of mixed biomaterial.

19 Claims, 8 Drawing Sheets

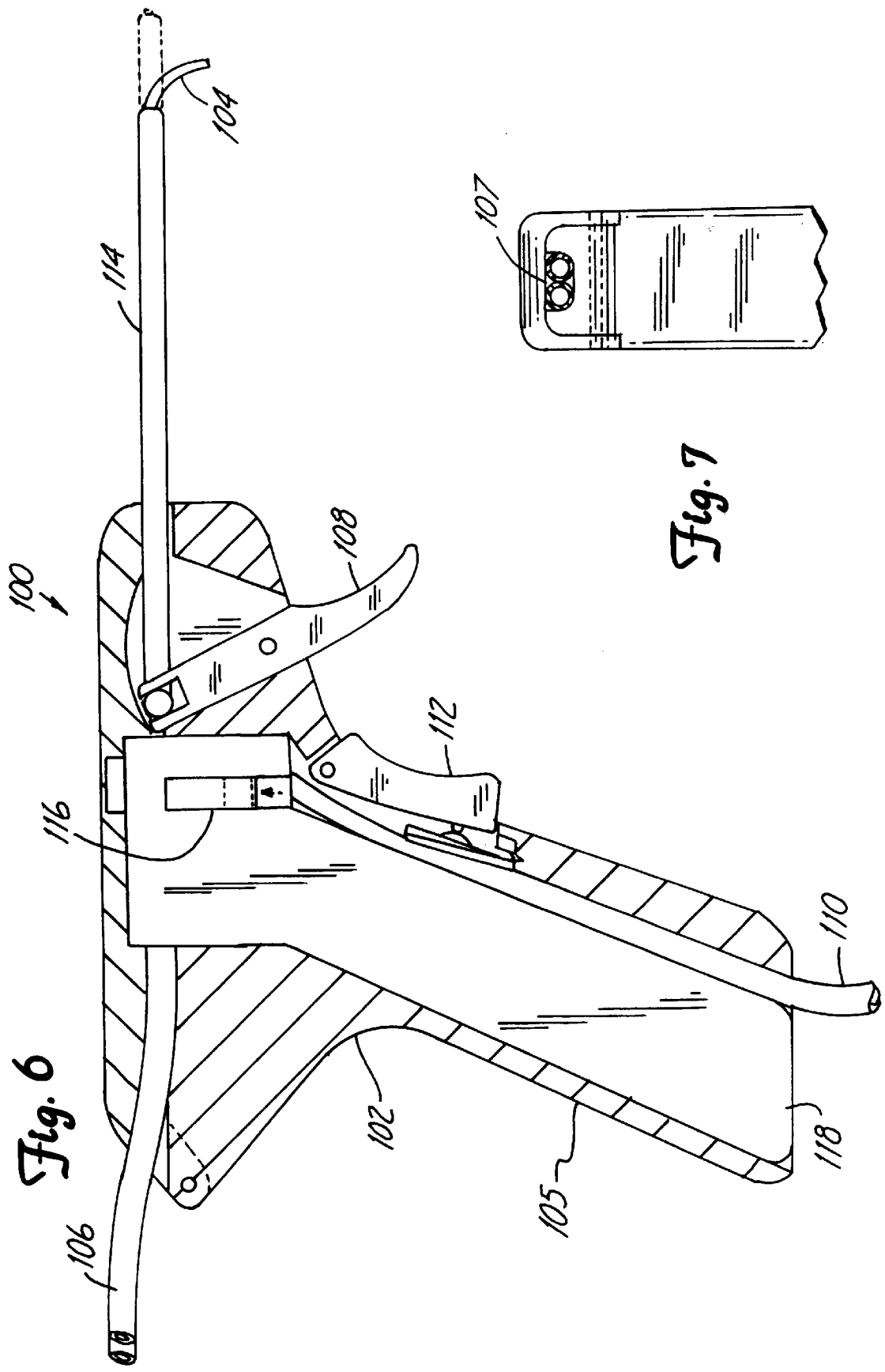

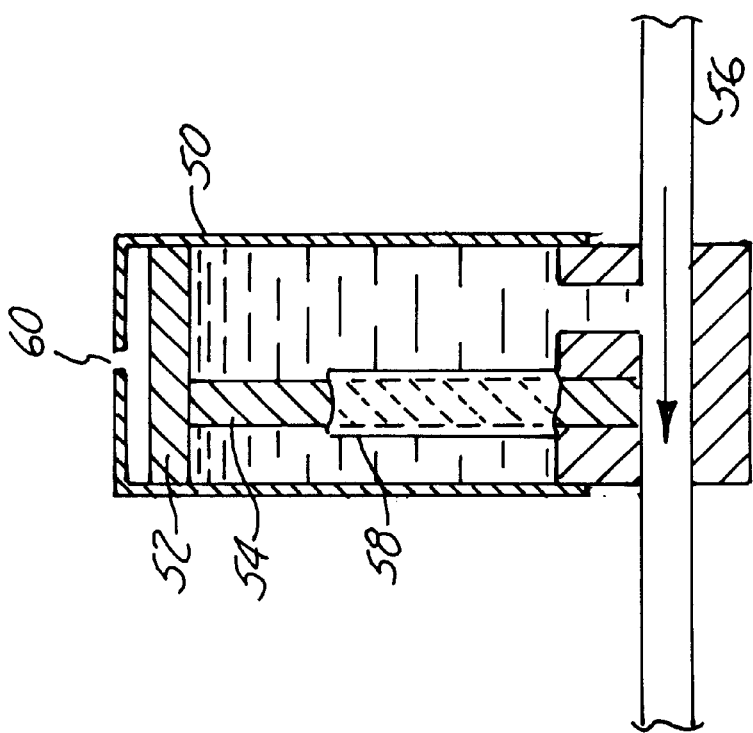
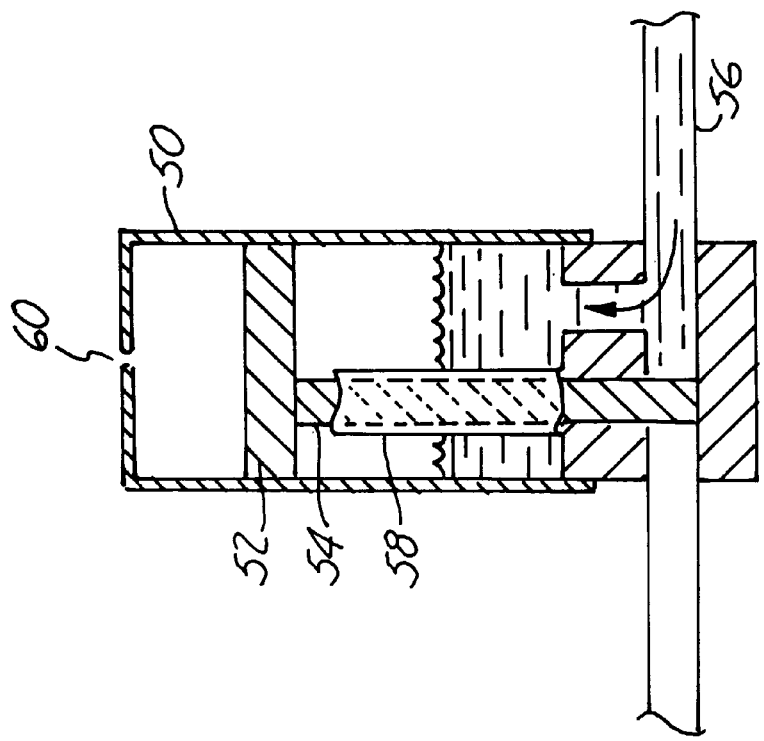

STATIC MIXER

CROSS REFERENCE TO RELATED APPLICATIONS

This application is a continuation-in-part of U.S. patent application for BIOMATERIAL SYSTEM FOR IN SITU TISSUE REPAIR, filed Dec. 18, 1997 and assigned U.S. Ser. No. 08/993,468.

TECHNICAL FIELD

This invention relates to mixing devices for polymerizable resins. In another aspect, the invention relates to devices for mixing and delivering curable materials to parts of the body, e.g., in the course of surgical or other techniques.

BACKGROUND OF THE INVENTION

Multiple-part curable resins (e.g., epoxies and dental restorative resins) are commonly dispensed and mixed using a multiple-barreled syringe equipped with an exit nozzle containing a static mixing element. The materials contained in the syringe are dispensed and mixed by depressing the syringe plunger, thereby forcing the resin components from the syringe barrels into the static mixing element (where the resin parts are intermixed with one another) and out the exit nozzle.

Similar apparatuses have been known in which fluids to be mixed have been dispensed by double barreled syringe or caulking gun type dispensers (see e.g. U.S. Pat. Nos. 3,309,814, 4,041,463, and 4,538,920). Dispensing devices of this general type, as is well known in the art, are useful in the application of a variety of pasty or highly viscous products such as adhesives, joint filler agents, foams, sealants, molding compounds etc. Such products typically consist of two or more components which are stored separately and mixed at the time of use in order to start a chemical reaction between them, usually causing a solidification or hardening of the resultant mass.

U.S. Pat. No. 4,767,026, for instance, describes a dispensing device and disposable mixer combination in which the dispenser stores the fluids separately and delivers them to an orifice in which the fluids are maintained in separation to the point of interface between the orifice. Other examples of mixing devices are described, for instance, in U.S. Pat. Nos. 5,566,860, 5,474,540, 5,071,040, 4,995,540, 4,846,373, 4,735,616, 4,676,657, 4,631,055, 4,359,049, 4,044,758, 4,040,420, 3,806,097 and 3,223,083.

On a separate subject, Applicant has previously described a system for resurfacing joint surfaces that includes the step of delivering a curable two-part biomaterial by minimally invasive means. See, for instance, U.S. Pat. No. 5,556,429 and PCT Application Nos. PCT/US97/00457 and PCT/US, the disclosures of each of which are incorporated herein by reference.

When used in such a minimally invasive method, e.g., to resurface or repair ajoint in situ, most if not all of the above-described commercial syringe assemblies suffer from several shortcomings, including the fact that the devices tend to be too long for convenient, ergonomic use. Generally, the length of the device is a function of the overall length needed to fully mixed the components. While not typically a concern when used for industrial or other applications, the overall length of conventional devices renders them difficult to use, e.g., awkward to position, manipulate and control, in the course of surgical procedures that require precise control and are performed by minimally invasive techniques under fiberoptic visualization.

Much of the overall length of a conventional device is required solely to provide a mixing path that is of sufficient length to thoroughly mix the components. The length of the mixing path is generally determined so as to provide sufficient mixing, on the one hand, and the ability to deliver the material before it sets, on the other. Rather than be concerned with overall length, the mixing efficiency of such devices can actually be improved by providing either a longer mixing path and/or improved geometries of the mixing elements themselves.

In the course of using such commercial devices for minimally invasive surgical procedures, Applicants have found that it would be highly desirably to have a device that provides several features that are not typically provided by the above described devices. Such features would include, for instance, automated and/or single-handed control and operation, as well as the ability to control the device in sufficient proximity to the surgery site to facilitate ergonomic control while preventing premature curing of the biomaterial. What is needed, therefore, is a device that can be used to mix and deliver multiple part curable systems in a manner that addresses the unique and demanding surgical needs set forth above.

SUMMARY OF THE INVENTION

The present invention provides a device for mixing and delivering a curable biomaterial, the device comprising:

(a) an attachment site for a biomaterial source, the source comprising a plurality of biomaterial components adapted to be mixed in order to initiate cure, (b) a body portion comprising
  i) a handle for gripping and actuating the device, and
  ii) a biomaterial mixing path having inlet and exit ends, the inlet end of the mixing path adapted to be placed in fluid communication with the biomaterial component source, the mixing path being adapted to combine and mix the components within a time suitable to permit the mixed components to traverse the mixing path in a flowable fashion, and within an longitudinal distance adapted to provide controllable, ergonomic operation in the course of minimally invasive surgery, and (c) a delivery unit comprising a delivery conduit having an inlet end in fluid communication with the exit end of the mixing path, and an exit end adapted to deliver the mixed biomaterial to a tissue site.

A preferred device is adapted to optimize its ergonomic and controllable operation in the course of minimally invasive surgery, providing the surgeon with improved control and tactile sense in the course of biomaterial delivery. Surprisingly, Applicants have discovered the manner in which suitable mixing of a viscous biomaterial can be accomplished within a suitable time and a shorter longitudinal distance than possible with available commercial mixing devices. Such attributes, in turn, provide a device that is sufficiently short for ergonomic use in minimally invasive surgery, without unduly sacrificing mixing efficiency. Optionally, and preferably, portions of the device (in particular, those that do not contact biomaterial) can be made reusable in order to minimize waste and cost.

In its various embodiments, the overall longitudinal distance contributed by the mixing path of a present device is typically on the order of one-third, preferably one-fifth, and most preferably one-tenth, or less, of the overall length of the mixing path itself, thereby contributing greatly to the improvement in ergonomic control afforded by such a device.

In a preferred embodiment, the present device includes a delivery unit that comprises the delivery conduit itself together with other optional features, such as an overflow shunt or reservoir for diverting the initial and/or later amounts of mixed biomaterial from the tissue site. As another optional feature, the delivery unit can include a retractable sheath for covering the delivery conduit in order to facilitate its entry and placement into the body.

Ideally, some or all of these features can be actuated by one-handed operation of the device, and preferably using only the thumb and index fingers, including a mechanism for actuating the delivery and mixing of the biomaterial components, a mechanism for controllably shunting mixed biomaterial from the delivery conduit, and a mechanism for extending and/or retracting the delivery conduit and/or a protective sheath. In a particularly preferred embodiment, the controls are of sufficient symmetry or alignment (e.g., aligned along the central plane of the device) in order to facilitate either right-handed or left-handed operation.

In a particularly preferred embodiment, such as the repair of a knee joint, the biomaterial is a two-part curable polyurethane, the mixing path comprises a plurality of static mixing elements, and the delivery conduit is provided in the form of a preformed (e.g., curved), pliable material in order to facilitate the delivery of the biomaterial to the site of anchor points previously established within the bone.

In another aspect, the preferred device provides an attachment mechanism for attaching a biomaterial source in a controllable, flowable fashion. For instance, the biomaterial source can either by physically attached to the body portion (e.g., in the form of cartridges) or remote from the body portion and attached by tubing. In the case of direct attachment the body portion will typically provide an attachment site in the form of a receptacle for a biomaterial component pack or cartridges. In the case of remote attachment, the body portion will typically provide an attachment site in the form of connections for tubing that, in turn, is flowably attached to the biomaterial source.

Various components of the device, as well as the device itself and biomaterial source can be manufactured, sterilized, and sold alone, or sold together in a kit, e.g., with the biomaterial source being attached to the device at the time of use to form a delivery system. In another alternate embodiment, the invention provides a biomaterial source per se, for instance in the form of a canister or cartridge pack, adapted to be attached to a device as presently described.

In yet another aspect, the invention provides a method of delivering an in situ curable biomaterial to a tissue site, the method comprising the steps of accessing and preparing the tissue site using minimally invasive techniques; providing a biomaterial delivery system comprising a delivery device and biomaterial source; positioning the delivery conduit of the device into the tissue site using minimally invasive techniques; mixing and delivering the biomaterial to the tissue site, and curing the biomaterial in situ to provide a permanent replacement for natural tissue.

BRIEF DESCRIPTION OF DRAWING

A preferred embodiment of the invention is illustrated in the accompanying drawing, in which:

FIG. 6 is a vertical sectional view of the device of FIG. 5, showing portions in fall, and showing the retractable sheath in both a retracted position (full line) and extended (dotted line) position;

FIG. 7 shows a rear view perspective of a portion of the device shown in FIG. 5;

FIG. 9(a) and (b) show an alternative embodiment of a shunt for use in diverting the initially mixed stream of biomaterial in a device of the present invention.

DETAILED DESCRIPTION

Figure 1:
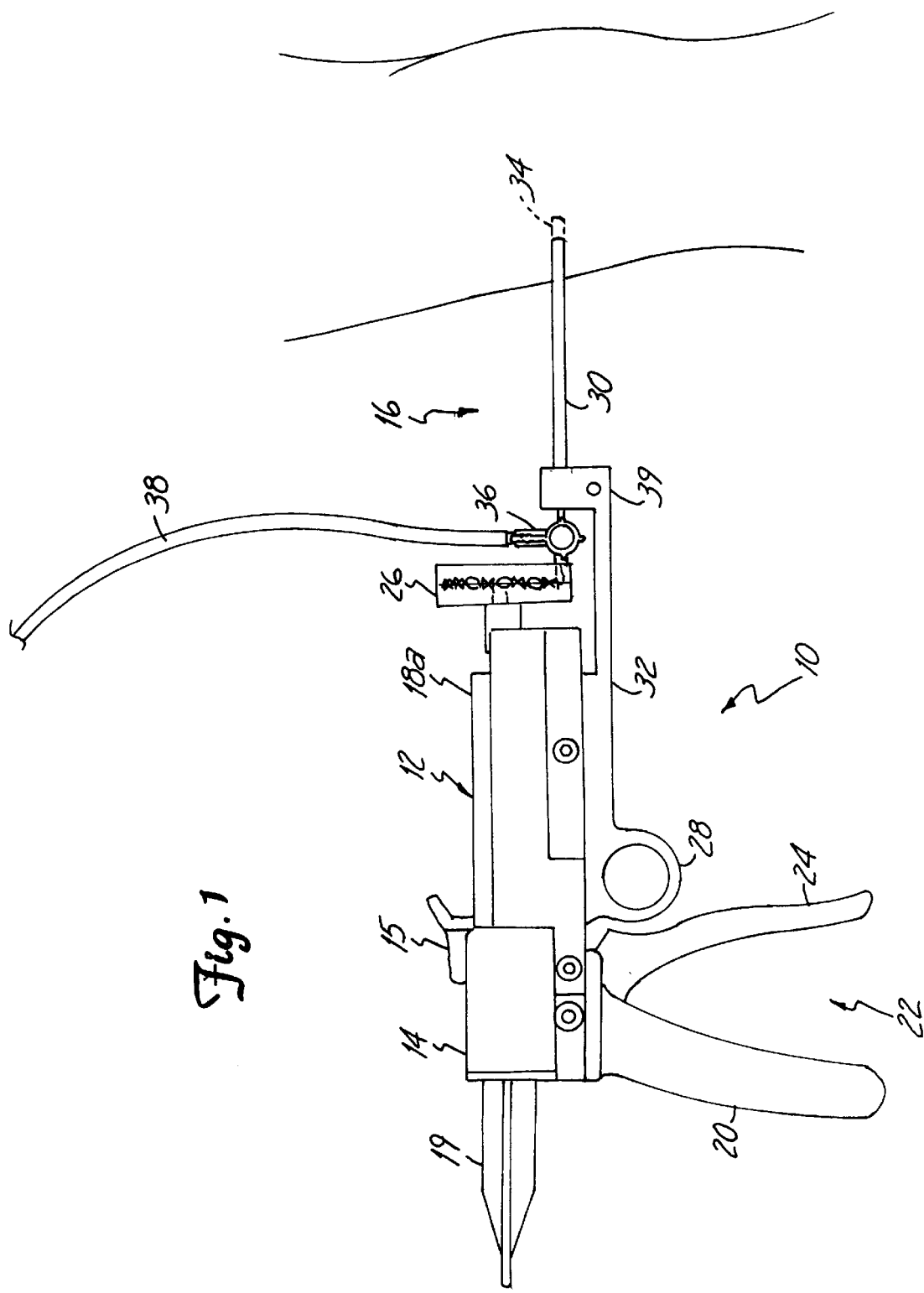
FIG. 1 is an overall schematic view of a system that includes one embodiment of a delivery device of this invention, showing the delivery conduit in a retracted position.

A device of the present invention is particularly well suited for use in delivering a curable biomaterial composition by minimally invasive techniques to a tissue site within the body. As used herein the following words and terms shall have the meanings ascribed below:

"repair" will refer to the use of a composition to augment, replace or provide some or all of the structure or function of natural tissue in vivo, for instance, to provide an implant such as a catheter, or to repair (e.g., reconstruct or replace) natural tissue such as cartilage, e.g., fibrocartilage or hyaline cartilage present in a diarthroidal or amphiarthroidal joint. Repair can take any suitable form, e.g., from patching the tissue to replacing it in its entirety, preferably in a manner that reconstructs its natural or other desired dimensions;

"cure" and inflections thereof, will refer to any chemical, physical, and/or mechanical transformation that allows a composition to progress from a form (e.g., flowable form) that allows it to be delivered to the joint site, into a more permanent (e.g., cured) form for final use in vivo. When used with regard to the method of the invention, for instance, "curable" can refer to uncured composition, having the potential to be cured in vivo (as by catalysis or the application of a suitable energy source), as well as to a composition in the process of curing (e.g., a composition formed at the time of delivery by the concurrent mixing of a plurality of composition components). As further described herein, the cure of a composition can generally be considered to include three stages, including (a) the onset of gelation, (b) a period in which gelation occurs and the composition becomes sufficiently tack-free to permit shaping, and (c) complete cure to the point where the composition has been finally shaped for its intended use;

"minimally invasive" refers to surgical techniques, such as microsurgical or endoscopic or arthroscopic surgical techniques, that can be accomplished with minimal disruption of the pertinent musculature, for instance, without the need for open access to the tissue injury site or through minimal incisions (e.g., incisions of less than about 4 cm and preferably less than about 2 cm). Such techniques are typically accomplished by the use of visualization such as fiberoptic or microscopic visualization, and provide a post-operative recovery time that is substantially less than the recovery time that accompanies the corresponding open surgical approach; and "mold" will refer to the portion or portions of an apparatus of the invention used to receive, constrain, shape and/or retain a flowable biomaterial in the course of delivering and curing the biomaterial in situ. A mold may include or rely upon natural tissues (such as the annular shell of an intervertebral disc) for at least a portion of its structure, conformation or function. The mold, in turn, is responsible, at least in part, for determining the position and final dimensions of the cured prosthetic implant. As such, its dimensions and other physical characteristics can be predetermined to provide an optimal combination of such properties as the ability to be delivered to a site using minimally invasive means, filled with biomaterial, and optionally, then remain in place as or at the interface between cured biomaterial and natural tissue. In a particularly preferred embodiment the mold material can itself become integral to the body of the cured biomaterial.

Biomaterial Source

Biomaterials suitable for use in the present invention can be provided in any suitable form, e.g., as two or more individual components. Some or all of these components can be provided either within or upon the body portion itself (e.g., in attachable syringe cartridges) or remote therefrom (e.g., as canisters attached or attachable by tubing to the body portion itself). The onset of flow of the components, and in turn their mixing, is preferably controlled by the user, e.g., by actuating a mechanical delivery means or by making electrical contact. In a further preferred embodiment, e.g., the invention provides for a plurality of different biomaterials, the delivery of any or all being connectable and controllable by the user. Optionally, the user can control the types or relative amounts of various components being delivered, e.g., to provide for mixed biomaterial compositions having different desired (cured or curing) properties. The components for a two-component biomaterial source, for instance, can be predetermined to be mixed in any suitable order and ratio, e.g., in a 1:1 (volume to volume) ratio, or between about 1:10 or 10:1.

The term "biomaterial source", as used herein, will refer to the actual component containment vessels (e.g., canisters or syringes) themselves, as well as associated supports, tubing, controls and the like, for use in attaching the containment vessels to the body portion and delivering their contents to the inlet end of the mixing path. In turn, a device of this invention can be manufactured, used and sold either with the biomaterial source in attached or attachable form (e.g., in the form of the syringes described herein), or without the biomaterial source (e.g., in the form of the gun assembly described herein). In the event the device is provided without the biomaterial source, the user will typically provide a separate single-use or stock supply of the biomaterial, which will be attached to the device at or near the time of use. In such a case, the biomaterial source can be flowably attached to the device at the time of use and in a sterile manner.

Body Portion.

The body portion of a device of this invention typically includes both a handle, for use in gripping and actuating or manipulating various features of the device, and a biomaterial mixing path. The term "body portion", as used herein, will generally refer to the portion or portions of the device other than the biomaterial component source and the delivery conduit (or their associated components). In turn, the body portion provides a biomaterial flow path that begins upon initial mixing of biomaterial components, and ends with the fully mixed components being delivered from an outlet end (e.g., cannula orifice) of the device. The mixing path, in turn, will typically provide one or more motionless static mixing elements positioned along a conduit of sufficient dimensions (e.g., cross-section and length) for its intended use. Optionally, the body portion can also include ancillary features and mechanisms such as a biomaterial heating element, controls for actuating the device, for retracting the protective sheath, for controlling the shunting of undelivered (e.g., initial) biomaterial, and the like.

The body portion can incorporate both reusable and disposable portions, which can be either preformed together and/or adapted to be detachably coupled to provide a sealed biomaterial flow path. Typically, the disposable portions include those components and surfaces that come into actual or potential contact with the biomaterial, or its components, in the course of use. While such portions can optionally be cleaned and re-sterilized, it is preferred that they be used a single time.

The body portion preferably provides an attachment site for releasably attaching the biomaterial component source to the inlet end of the mixing path, in order to provide for fluid communication between them. The biomaterial mixing path, in turn, is adapted to combine and mix the components within a time suitable to permit the mixed components to traverse the mixing path, and the delivery conduit, in a flowable fashion. While the inlet end of the mixing path is adapted to be positioned in fluid communication with a biomaterial component source, its outlet end is adapted to be positioned in fluid communication with a delivery unit that includes the delivery conduit. Preferably, some or all of the components of the present device, and particularly those containing the mixing path elements, are substantially transparent or translucent in a manner sufficient to permit the biomaterial to be visualized as it progresses through the device.

The mixing path is further adapted to combine and mix the components within a longitudinal distance suitable to provide controllable, ergonomic operation in the course of minimally invasive surgery. In a preferred embodiment the mixing path comprises a static mixing path flowably positioned between inlet and outlet ends of the mixing conduit, e.g., in the form of a plurality of mixing elements configured to produce a substantially homogeneous mixture of components. Given the present description, those skilled in the art will be able to determine the manner in which the actual dimensions and configuration of the mixing path can be varied according to the composition of the biomaterial, e.g., in view of the viscosity of the components and/or mixed composition, its cure characteristics (e.g., time to onset of gelation) and the extent of mixing required.

For instance, with a preferred composition of the type described herein, a mixing path will typically contain between about 10 and about 100 elements, preferably between about 20 and about 50 elements, and most preferably between about 30 and about 40 elements. These elements are positioned within a flow path of about 10 cm to about 50 cm, and more preferably about 20 cm to about 30 cm in overall length. Finally, the width of such a flow path is preferably between about 0.1 cm to about 2 cm, and more preferably between about 0.5 cm and about 1 cm. In such an apparatus, the mixed composition can be delivered to a tissue site within about one to about 10 seconds of initial mixing (and preferably within about 2 to about 5 seconds), and within a longitudinal distance of between about 5 cm and about 20 cm (and more preferably with about 10 cm and about 15 cm). The term "longitudinal distance", as used in this respect, refers to the shortest overall distance between the inlet end of the mixing path and the outlet end (orifice) of the delivery conduit. Preferably the portion of the longitudinal distance actually contributed by the mixing path is relatively small, e.g., on the order of about 1 to about 5 cm, with the remainder of that distance being provided, for instance, by optional shunting mechanisms and the cannula itself. The length of the cannula, in particular, can be adapted, on a joint by joint basis, in order to optimize control of the device, e.g., by balancing the respective lengths of those portions intended to pass into, or remain outside of, the entry portal.

A preferred device of this invention provides a mixing path configured in such a way that its contribution to the overall length of the device (i.e., the longitudinal mixing distance) is significantly less than the overall length of the mixing path itself. In turn, and depending on the configuration of the mixing path itself, the longitudinal distance contributed by the mixing path is typically on the order of one-third, preferably one-fifth, and most preferably one-tenth, or less, of the overall length of the mixing path itself. Most preferably, the longitudinal mixing distance approaches the width of the mixing conduit itself (e.g., as achieved in a spiral wound configuration), or multiples of the conduit width (as achieved by a single hair pin loop configuration), as both are described herein.

In one embodiment, the mixing path is provided in the form of a cylindrical bore of substantially uniform cross-sectional area, the bore containing a plurality of static elements to provide helical flow path along the length of the bore. The cylindrical bore can take any suitable form, e.g., it can be provided in a planar spiral configuration (e.g., wound in a watch spring configuration emanating from a common axis), or in a planar, overlapping configuration (e.g., bent back upon itself in a zigzag configuration).

A preferred device is configured to optimize its ergonomic and controllable operation in the course of minimally invasive surgery. Surprisingly, Applicants have discovered the manner in which suitable mixing can be accomplished within a shorter longitudinal distance than heretofore known, given the inherent characteristics of preferred biomaterials (e.g. viscosity and cure rate), in order to facilitate operation of the device. Applicants have found an optimal combination of mixing efficiency and overall length, and in turn, provide a device that is sufficiently short for ergonomic use in minimally invasive surgery, without unduly sacrificing mixing efficiency.

Such a device preferably provides single-handed control of most, if not all, features, including single-handed controls for actuating the delivery and mixing of biomaterial components, for extending and/or retracting the protective delivery sheath, and for controlling the shunting of mixed biomaterial. The style and location of such controls can be optimized to provide a desirable combination of such features as location, ease of use, and controllability in the course of arthroscopic or other minimally invasive procedures. The delivery of the biomaterial can be actuated using any suitable means, examples of which are described in greater detail below, including by depressing a plurality of plungers within corresponding syringes, or by electronically controlling employing remote pumps and reservoirs that are flowably connected to the body portion by tubing.

In the embodiment in which the biomaterial source (e.g., a syringe cartridge) is attached to the body portion, delivery from the source can be accomplished using any suitable means. In one preferred embodiment, the biomaterial is secured within the body portion, e.g., by placing it into a receptacle and securing it with a lock or cover. A corresponding plunger is positioned within the end of the syringe cartridge, the plunger being adapted (e.g., with gear engaging teeth along the length of its lower surface) to engage a corresponding gear provided by the body portion itself. The gear, in turn, is rotatably connected to a clutch assembly within the body portion, that can be actuated and controlled by the user in order to drive the plungers into the syringes.

The contents of the syringe can be sealed prior to use by placing plunger seals (and plungers, if desired) in the open ends of the syringe barrels. The syringe outlet can be sealed by providing a snip-off plastic molding at the outlet end of the syringe. Alternatively, and preferably, the outlet end of the syringe is sealed with a removable cap equipped with an appropriate locking mechanism. If the exit conduit is attached to the syringe using a bayonet mount, it is preferable to employ a similar bayonet mount on the removable cap. Such a cap can then be reinstalled on the syringe between uses thereof.

Suitable and preferred examples of such clutch assemblies can be described as 'drawn cup roller clutches" and are available, for instance, from The Torrington Company, Torrington, Conn. (e.g., as "Type DC" roller clutches). Such a clutch transmits torque between a shaft and body portion in one direction (driving the plungers into the syringe) and allows free overrun in the opposite direction. When transmitting torque, either the shaft or body portion can be the input member. The unit thereby permits indexing, backstopping or overrunning. The clutch uses a low profile radial section as drawn cup needle roller bearings, and provides a unit that is compact, lightweight, and able to be operated directly on a hardened shaft. Moreover, the unit can be easily mounted, e.g., with a simple press fit within the body portion. The precisely formed interior ramps provide surfaces against which the rollers wedge to positively lock the clutch with the shaft when rotated in the proper direction. Transition from the overrun to locked operation normally occurs with minimal lost motion (backlash).

Such clutches provide interior ramps which control the lockup and free run of the clutch, and which are formed during the operation of drawing the cup. The ramps are sufficiently hardened to assure sufficient strength and wear. Molded clutch cup cages can be provided in a variety of styles, including as a one-piece cage of acetal resin plastic with integral leaf style springs, or with a glass fiber reinforced nylon cage equipped with inserted stainless steel leaf springs. The springs are thought to permit higher rates of engagement, and achieve a greater spring life. One particular advantage of a clutch as presently described includes the fact that the clutch mechanism within the body portion remains substantially free from contact with biomaterial components. This, in turn, facilitates the ability to clean, re-sterilize and re-use the body portion with a new syringe and plunger combination.

The on/off control can be in any suitable form, e.g., a trigger, button or switch, that can be used to begin the delivery of biomaterial components from the biomaterial source to the inlet end of the mixing path. Where the biomaterial source is remote from the body portion itself, e.g., in the form of cannisters or vessels connected by tubing, the on/off control can include electrical switching means for actuating an associated pump. In other embodiments, the biomaterial source is attached or attachable to the body portion itself, e.g., in the form of a plurality of syringe barrels of the type described herein. A suitable on/off control for use with the barrel-type device is in the form of a trigger-actuated plunger mechanism as described herein. The on/off control is generally used to control the pressure needed to deliver the components to the mixing path, but also through the path itself, as well as into and through the delivery conduit. Those skilled in the art will appreciate the manner in which that pressure can be determined by such factors as the viscosity of the various flowable materials, the overall distance that they must flow, the cross-sectional area of the flow path, and the desired delivery rate.

Other desirable controls include means for controllably shunting mixed biomaterial from the delivery conduit. The shunting mechanism can include a fingertip control, e.g., slide or button type, for shunting desired portions (e.g., the initial or final streams) of mixed biomaterial from the delivery conduit. Generally, such a control will serve to divert the flow path of mixed biomaterial, beyond the outlet end of the mixing path, into a plurality of directions.

It is also preferred that a device of this invention provide a mechanism for extending and/or retracting the delivery conduit and/or a protective delivery sheath. The mechanism can include the retractable sheath itself, and an associated single-handed control, that can be used to cover some or all of the delivery conduit in order to facilitate its entry and placement into the body.

The device can also provide a warming mechanism, together with associated controls, for use in warning the biomaterial components in their separate and/or mixed forms, in order to facilitate or affect their flow or cure characteristics.

Finally, the body portion also provides an attachment mechanism for sealably attaching the outlet end of the mixing path to the inlet end of the delivery conduit. The attachment mechanism can be provided in any suitable form to provide a detachable and suitably sealed flow path between the two. The delivery conduit, for instance, can be provided upon a support that is attached to the body portion by a sliding, rotating, and/or pushing motion, in order to provide a continuous flow path between the mixing path and the delivery conduit. The delivery conduit can be either permanently or releasably attached or attachable to the outlet end of the mixing path.

Other optional features of the device include a mechanism for changing either the biomaterial source, or the relative amounts of components being delivered and mixed, or for changing some or all of the components themselves in the course of use (e.g., with the delivery conduit positioned within a tissue site). Such a mechanism can be used to provide cured biomaterials having varying properties, e.g., varying degrees of cure or varying physical or chemical properties, or for delivering entirely different materials, e.g., different biomaterials or different primers or coating compositions. Such a mechanism will generally include a mechanism for attaching whatever sources of such compositions may be desired, and/or a mechanism for flushing and shunting the delivery path with subsequent formulations, and shunting the void volume or flush volumes.

Delivery Unit

The delivery conduit provides an inlet end adapted to be positioned in fluid communication with the outlet end of the mixing path, and an outlet end adapted to deliver the mixed biomaterial to a tissue site. As used herein, the term "delivery unit" will include the actual delivery conduit, as well as other optional features, such as a mechanism for attaching the unit to the body portion (e.g., to the outlet end of the mixing path), a retractable sheath, and shunt, as described herein. Typically it will be the delivery unit will be attached or attachable to the body portion, at the time of attaching the biomaterial source, in order to provide a sealed flow path and controllable operation.

Generally, the outlet end of the delivery conduit is configured to deliver mixed biomaterial to a desired site within the body; the tip being dimensioned (e.g., of suitable length and diameter) to be placed within an internal joint site by minimally invasive means, and controlled outside the body. In one preferred embodiment, the delivery conduit is in the form of a curved, elastomeric, pliable polymeric material such as polyamides (e.g., Nylon®) or polyether block amide resins available from Elf Atochem under the tradename Pebax®. Such resins are thermoplastic elastomers combining the properties of nylon and rubber. The Pebax® resin structure consists of a regular linear chain of rigid polyamide segments interspaced with flexible polyether segments. Because of compatibility between the blocks, Pebax® resin exhibits a two-phase structure: crystalline (polyamide) and amorphous (polyether), allowing it to behave both as a thermoplastic and as an elastomer. As a result, it is possible to modify the physical, chemical, and thermal properties of Pebax resin through the appropriate combination and amounts of polyamide and polyether blocks.

Such materials can be fabricated to have any desired dimensions, e.g., having an outer diameter of between about 2 mm and about 10 mm, being curved with a radius of between about 5 and about 15 mm, and having a tapered tip. The actual dimensions will typically depend on the application, e.g., the joint to be resurfaced. The joint, in turn, and particularly the extent of distraction applied, will generally define the dimensions of the working environment. In the knee, for instance, Applicants have found that a conduit of this nature facilitates the delivery of the biomaterial to the site of anchor points previously established within the bone. Given a distracted joint space of about 1 cm, for instance, the delivery orifice of the conduit tip is preferably adapted to be positioned into and manipulated within that space, yet be able to deposit biomaterial into an anchor point at substantially a right angle to the angle of the conduit itself.

Optionally, the delivery conduit can be provided in a form that facilitates its attachment, at its outlet end, to another conduit (e.g., one connected to an implanted or implantable mold apparatus), or to the mold apparatus itself. In another optional embodiment, the delivery conduit can be provided with gradations or markings for use in determining distances or the approximate depth of anchor points associated with the surface or area to be filled.

Certain preferred embodiments of this invention will be described with reference to the Drawing, wherein FIGS. 1 through 4 provide an example of a device having the biomaterial source attached or attachable to the body portion itself, and FIGS. 5 through 9 show an example of a device adapted to be attached to a remote source of biomaterial.

FIG. 1 shows a side elevation view of a system 10 of the present invention, including biomaterial source 12, body portion 14, and delivery unit 16. As shown, biomaterial source 12 is provided in the form of two syringes 18a and 18b (the latter shown in FIG. 3), placed within a receptacle of body portion 14. The syringes are adapted to contain respective biomaterial components, which are maintained separately from each other prior to dispensing the components from the syringes. The syringes 18a and 18b can be placed within the body portion 14 by lifting latch 15, which is attached in a hinged fashion to the body of the housing. With the latch lifted, the syringes can be gently lowered into a retained relationship within a corresponding receptacle within the body portion 14. The latch 15 can then be lowered and locked in place, e.g., by a snap fit or other suitable mechanism, in order to secure the syringes in fluid communication to the inlet end of the mixing path. Corresponding pistons 19 are provided located within the syringe chambers, and are movable from their initial position adjacent the rear ends of the chambers toward the discharge end of the chambers, in order to simultaneously discharge the respective components from the interior of the chambers and into a congruent mass.

Figure 4:
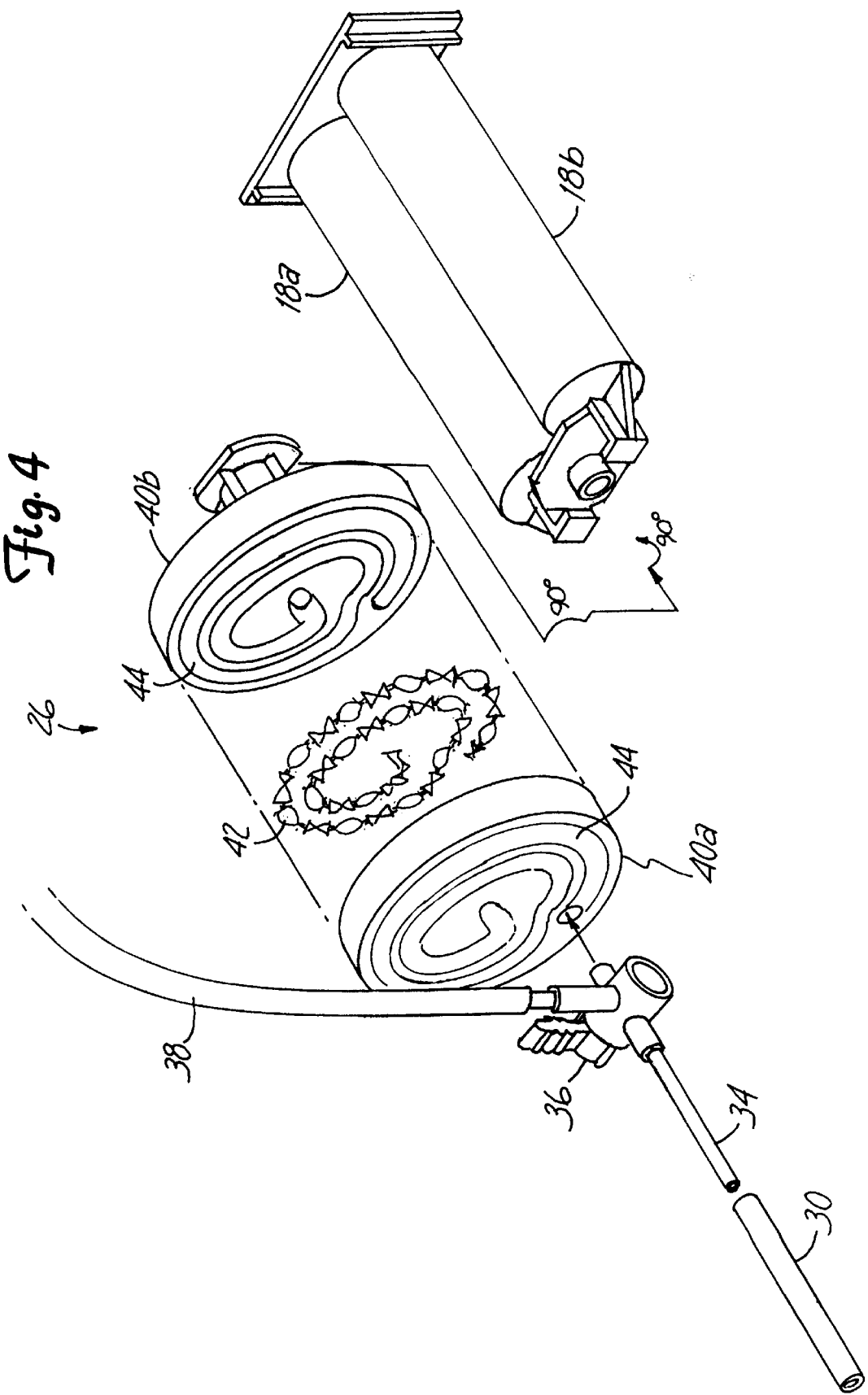
FIG. 4 is an exploded perspective view of certain components of the system of FIG. 1, showing the material-contacting parts in disassembled form.
Figure 5:
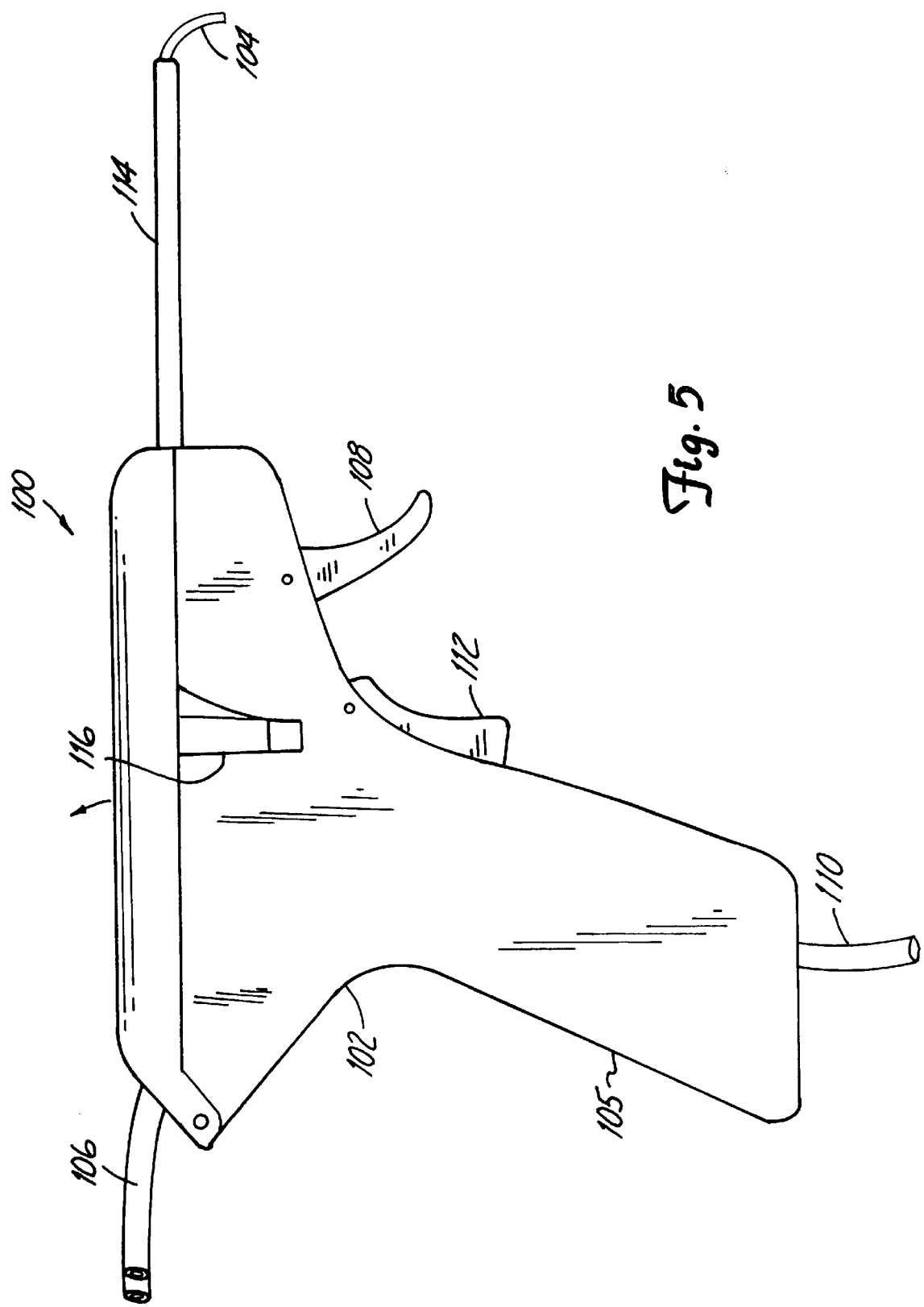
FIG. 5 is a side elevation view of an alternative embodiment of a delivery device of this invention.

As can be seen in FIG. 4, the syringes are provided in the form of two parallel internal chambers, separated by a barrier, each of which is intended to be filled with one part of a two-part polymerizable material, e.g., polymerizable resin. When a pair of pistons are forced into the chambers in syringe, the contents of the syringe exit via the respective outlet ends, through outlet passages, and into the static mixing path where they are intimately mixed to form a homogeneous mass which will cure following expulsion from the outlet of the exit conduit. Static mixing elements are provided in disc-like housing 26 adapted to assume the configuration of the mixing path.

Rotational alignment of the mixing path assembly with respect to the syringe is obtained using a suitable mounting means (e.g., a bayonet mount, threaded connections, frictional connections, splined or keyed fittings). When so mounted, the mixing path is fixably rotationally aligned with respect to syringe. The mixing path assembly can be readily removed and discarded after use by rotating the assembly approximately 90° counterclockwise (as viewed from the exit end of the conduit) and pulling the disc like housing away from the syringes.

Body portion 14 includes a pistol grip 20 that includes both the handle portion 22 and the trigger 24, for use in actuating the device. The body portion also provides a mechanism for retracting the delivery sheath 30 associated with the delivery unit 16, the mechanism including a finger loop portion 28 attached to a slidable portion 32, which in turn is adapted to be attached to the delivery sheath 30 in order to slide it back or forth along the delivery conduit 34. The slidable portion also includes a vice like thumb screw portion 39 that can be used to grasp and secure the sheath to the slidable portion. In addition to delivery conduit 34 and its protective retractable sheath 30, the delivery unit 16 also includes a disc-like body portion 26 that contains the static mixing elements 52 within a cylindrical path 44 formed by sealably attaching portions (40a and 40b), and a valve 36 capable of being manipulated in order to divert the stream of mixed biomaterial, prior to and following delivery to the tissue site itself, to outlet shunt 38. The inlet end of the cylindrical housing is positioned in fluid communication with the outlet end of the syringes, such that the two biomaterial components are simultaneously combined and begin to mix.

Figure 2:
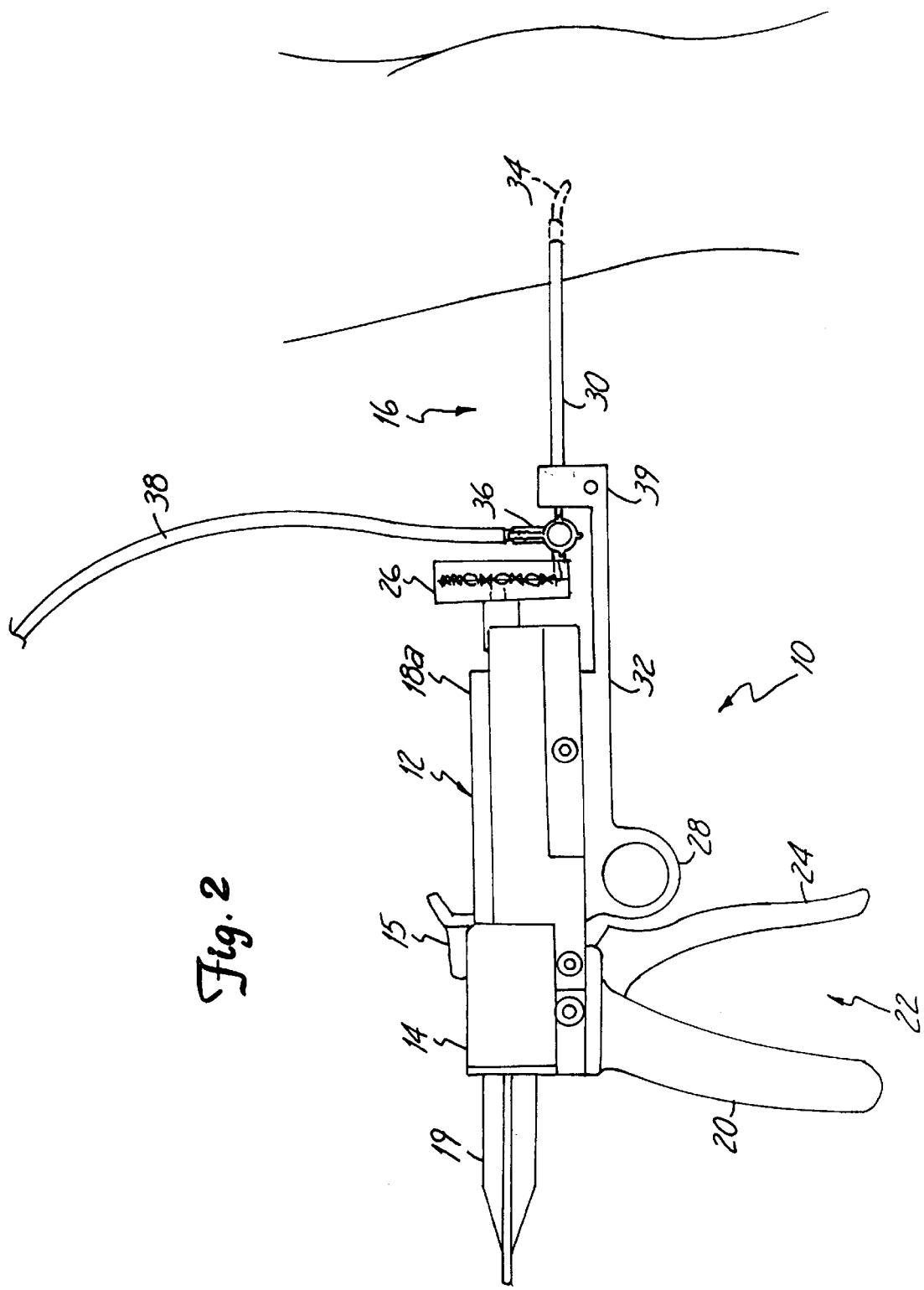
FIG. 2 shows the system of FIG. 1 with the delivery conduit extended.
Figure 3:
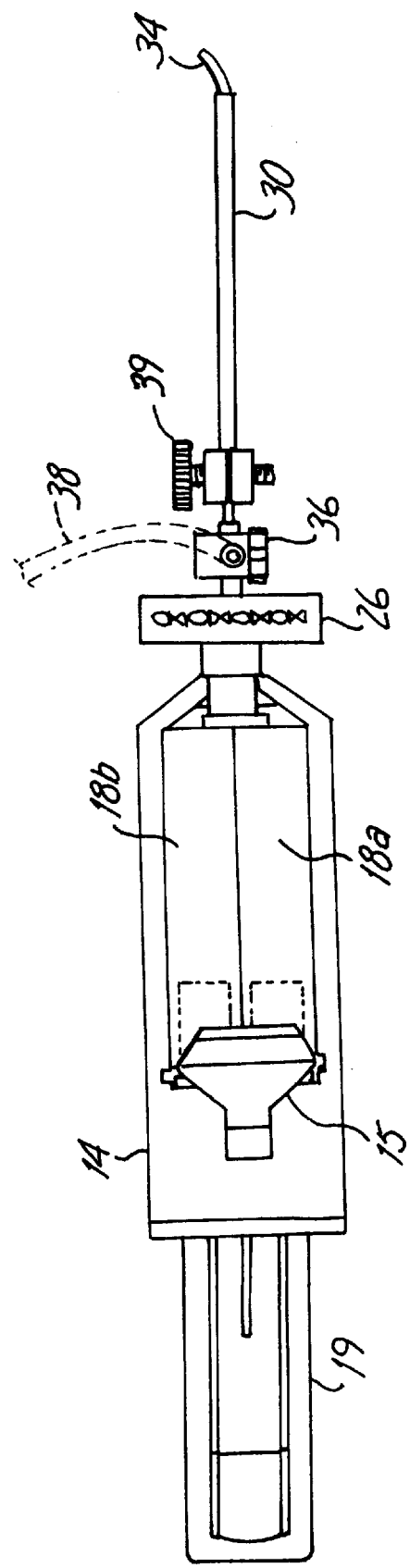
FIG. 3 is a top plan view of the system of FIG. 2.

FIG. 2 shows the system of FIG. 1 with the slidable portion, and in turn delivery sheath 30, in their retracted positions in order to expose the curved, pliable tip of delivery conduit 34. FIG. 3 provides a top plan view of the apparatus shown in FIG. 2, showing both barrels (18a and 18b) of the biomaterial-containing syringes, as well as the body portion 14 and delivery unit 16.

FIG. 4 is an exploded perspective view of system of FIG. 2, showing the major biomaterial-contacting components of the device in disassembled form. These components include, in the direction of flow, the syringe barrels 18a and 18b of the biomaterial source 12, the paired portions of cylindrical housing (40a and 40b) of the body portion 40, and the static mixing elements themselves 42, which are dimensioned to lay within cylindrical groove 44 formed upon recombining housing portions 40a and 40b. Also shown is valve 36 that can be manipulated to direct the mixed biomaterial to either outlet shunt 38 or delivery conduit 34, covered by retractable sheath 30.

In use, upon actuating the trigger the two biomaterial components contained in the syringe are expelled from their respective syringes, initially as two contiguous streams of resin, and upon contact in the form of a co-extruded two-layered mass. The resins pass from the syringe barrel through the syringe outlet and toward the static mixing element. The two resin streams impinge upon the first mixing blade of the static mixing element and are split or subdivided into a mass containing two new streams of resin, preferably with each new stream containing one-half of each of the two incoming streams.

Thereafter, the stream traverses the length of the helical mixing path, undergoing further mixing with each additional pass of an auger blade provided by the static elements. Finally, the mixed stream is extruded into and through the delivery conduit. Optionally, and preferably, the delivery conduit is dimensioned to be inserted using minimally invasive techniques into the body in order to deliver the stream under fiberoptic visualization to a desired site, such as a joint or internal mold.

FIGS. 5 through 8 show an alternative preferred embodiment of a device 100 of the present invention, including body portion 102 and delivery conduit 104. Tubing 106 can be connected to the device in order to provide operable, fluid communication between the fluid flow path and a remote source of biomaterial components (not shown). As shown, the device also includes an actuating trigger 112 that provides for electrical contact employing an attachable power cord (not shown), in order to begin and control the flow of biomaterial components into and through the device to the delivery unit. With power supplied to the syringes by means of a lead screw and stepper motor (not shown), other optional features can include an automatic purge cycle, controlled volume delivery, audible tones, controllable suctioning of the biomaterial at the conduit orifice, and the like.

The device also includes a second trigger that is shown connected in a hinged relationship with delivery sheath 114. The second trigger 108 is adapted to be actuated in order to retract and/or extend sheath 114. The delivery sheath can be biased in the extended position, e.g., by the use of a spring (not shown), in which case the sheath can be extended during placement by temporarily depressing the trigger 108. Also shown is an outlet shunt 110 through which excess biomaterial can be shunted, before, during and/or after delivery to the tissue site, by actuating corresponding lever 116 associated with an internal valve mechanism.

Figure 8:
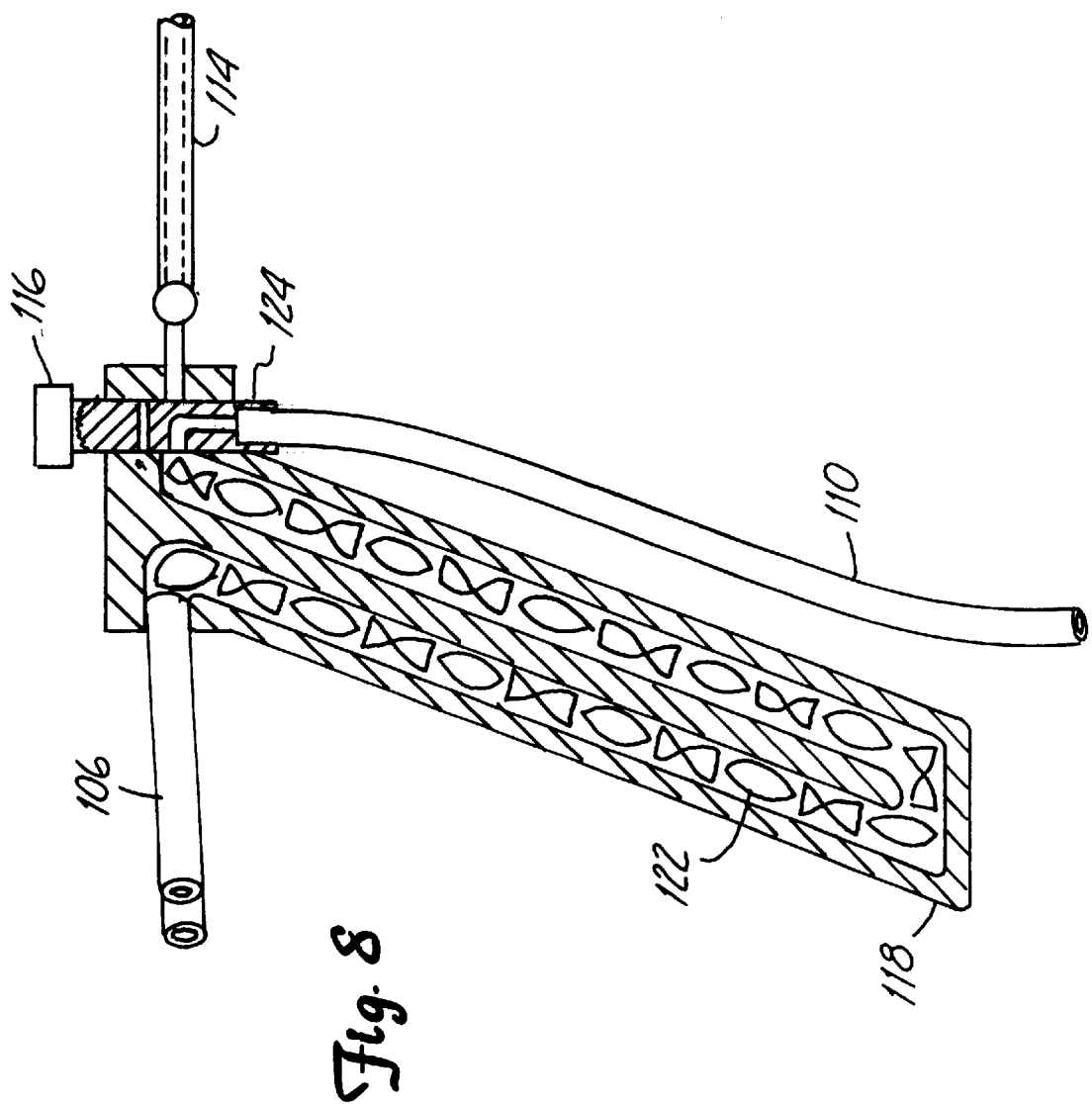
FIG. 8 shows a vertical sectional view through the portion (mixing path cartridge and valve mechanism) shown in full in FIG. 6.

FIG. 6 shows a partial sectional view of the device, with the mixing path cartridge shown is full in its position within body portion 102, whereas FIG. 8 shows a sectional view of the mixing path cartridge 118 itself. FIG. 7 shows a rear view of the device, including attachment site 107 for the attachment of the tubing from the remote canisters. In these figures, tubing 106 from the remote biomaterial source 12 is flowably connected to the path containing static mixing elements 122, and in turn, to the delivery conduit by means of a moveable shunt valve assembly 124. The valve assembly can be used to shunt flow of the mixed biomaterial as between the delivery conduit 104 and one or more other paths, including to a shunt tube 110 as shown. By positioning the flow path in a circuitous (e.g., hairpin) configuration within the handle grip, this embodiment provides an longitudinal distance that is far shorter than (e.g., on the order of one-tenth or less) the mixing path length itself.

Optionally, and as depicted in FIGS. 9a and 9b, the initial stream of mixed biomaterial can be shunted into a reservoir adapted to automatically divert the initial flow of biomaterial, and to then permit flow into the conduit after shunting a predetermined volume of the initially mixed biomaterial. An example of such a reservoir is shown in FIG. 9 in the form of a cylindrical reservoir 50 provided in fluid communication with the outlet end of the static element path and containing a plunger-like insert 52 coupled to shaft 54. The plunger is movably positioned within the cylinder, contacting its walls in a manner that substantially blocks the flow of biomaterial to the space above the plunger. In its initial position (9a), the lower end of shaft 54 is positioned in a manner that substantially blocks the flow path 56 between the mixing path and the delivery conduit. In turn, the initial biomaterial is directed (as shown by the arrow) into the reservoir itself in order to fill the cylinder.

Upon exiting the mixing path the initial stream of biomaterial first enters the cylinder below the plunger, causing it to enter and rise within the cylinder until the cylinder is filled, whereupon the plunger is lifted by positive pressure (fluid) such that the shaft (54) itself is lifted from its position within the flowpath, thereby opening the path for direct flow of biomaterial through the shunt unit and into the delivery conduit. Air vent 60 permits the release of air in order to facilitate the flow of biomaterial as the plunger rises. The volume within the reservoir 50 can be predetermined to assure that a sufficient volume of the initially mixed biomaterial is shunted, before delivery begins to the conduit. Preferably, measures are taken to ensure that the shaft is not prematurely lifted by biomaterial, e.g., by a tacky biomaterial that might adhere to the shaft and lift it before the reservoir is filled. Such measures can include, for instance, fabricating or treating the shaft from or with materials or coatings that substantially prevent the adherence of biomaterial. Such measures can also include the use of a sleeve (58) that substantially covers the shaft but that remains attached to the base of the reservoir. As such, the shaft itself is protected from direct contact with the biomaterial, at least until such time as the biomaterial has reached the top of the sleeve and begins to contact and raise the plunger.

Composition.

A device of the present invention can be used to mix and deliver a biomaterial composition having two or more parts, where the parts can be combined at the time of use in order to initiate cure. A preferred biomaterial composition for use in a device of this invention is a curable polyurethane composition comprising a plurality of parts capable of being sterilized, stably stored, and mixed at the time of use in order to provide a flowable composition and initiate cure. In a particularly preferred embodiment, the parts include: (1) a quasi-prepolymer component comprising the reaction product of one or more polyether polyols, one or more isocyanates, and one or more reactive hydrophobic additives, and (2) a curative component comprising one or more polyether polyols, one or more chain extenders, one or more catalysts, and optionally, other ingredients such as an antioxidant and dye. Upon mixing, the composition is sufficiently flowable to permit it to be delivered to the body using a device as described herein, and fully cured within the body under physiologically acceptable conditions. Preferably, the component parts are themselves flowable, or can be rendered flowable (e.g., by heating), in order to facilitate their mixing and use.

In a preferred embodiment, within the prepolymer, the polyether component is present at a concentration of between about 2% and about 10%, and preferably between about 4% and about 8% by weight, based on the weight of the composition, and is selected from the group consisting of linear or branched polyols with polyether backbones of polyoxyethylene, polyoxypropylene, and polytetramethylene oxide (polyoxytetramethylene), and copolymers thereof. A particularly preferred polyol is polytetramethylene oxide, preferably of relatively low molecular weights in the range of 250 daltons to 2900 daltons, and combinations thereof.

In a further preferred embodiment the isocyanate is present in excess in the prepolymer component, e.g., at a concentration of between about 30% and about 50%, and preferably between about 35% and about 45%, by weight. The isocyanate is preferably an aromatic (poly)isocyanate selected from the group consisting of 2,2'-, 2,4'-, and 4,4'-diphenylmethanediisocyanate (MDI), and combinations thereof. In such an embodiment, the reactive polymer additive itself is present at a concentration of between about 1% and about 50% by weight, and is selected from the group consisting of hydroxyl- or amine-terminated compounds selected from the group consisting of poybutadiene, polyisoprene, polyisobutylene, silicones, polyethylenepropylenediene, copolymers of butadiene with acryolnitrile, copolymers of butadiene with styrene, copolymers of isoprene with acrylonitrile, copolymers of isoprene with styrene, and mixtures of the above. In a particularly preferred embodiment the additive comprises hydroxyl-terminated polybutadiene, present at a concentration of between about 5% and about 30%, by weight, and preferably between about 5% and about 20% by weight.

In a further preferred embodiment, the polyether polyol of the curative component is as described above with regard to the prepolymer and is present at a final concentration of between about 20% and 60%, and preferably between about 30% and about 45%, by weight. In such an embodiment, the chain extender comprises a combination of linear (e.g., cyclohexane dimethanol ("CHDM")) and branched (e.g, trimethyloyl propane ("TMP") chain extenders, with the former being present at a final concentration of between about 1% and 20% (and preferably between about 5% and about 15%), and the latter being present at a final concentration of between about 1% and about 20%, and preferably between about 1% and about 10%, by weight of the final composition.

In a particularly preferred embodiment, a polymer system of this invention is provided as a plurality of component parts and employs one or more catalysts. The component parts, including catalyst, can be mixed to initiate cure, and then delivered, set and fully cured under conditions (e.g., time and exotherm) sufficient for its desired purpose. Upon the completion of cure, the resultant composition provides an optimal combination of properties for use in repairing or replacing injured or damaged tissue. In the course of curing, a suitable composition provides a bulk exotherm (within samples sizes suitable for in vivo use) of between about 100 degrees C and about 140 degrees C, and preferably between about 110 degrees C and about 130 degrees C, and a surface exotherm of between about 50 degrees C and about 80 degrees C, and preferably between about 60 degrees C and about 70 degrees C.

Additionally, a polymer system of the present invention preferably contains one or more, and more preferably two or more, biocompatible catalysts that can assist in controlling the curing process, including the following periods: (1) the induction period, (2) the setting period, and finally, (3) the final cure of the biomaterial. Together these three periods, including their absolute and relative lengths, and the rate of acceleration or cure within each period, determine the cure kinetics or profile.

The word "induction", and inflections thereof, when used in this respect refers to the time period between mixing or activation of one or more polymer components (under conditions suitable to begin the curing process), and the onset of gelation. In a method of the present invention, this period generally corresponds with the delivery of the biomaterial to the site of ultimate use. The induction period is characterized by infinitesimal or limited increase in viscosity of reacting mixture and relatively flat exotherm profile. Generally, a biomaterial of this invention is simultaneously mixed just prior to actual delivery into the joint site, providing the surgeon with sufficient time to add and position material (e.g., into anchor points) before gelation causes the material to become less easily workable. Thereafter, the surgeon can leave the material in place as it sets, e.g., for on the order of three to twenty minutes, before placing instruments back into the site to finish sculpting the implant, or performing other desired steps such as positioning the femoral condyles to shape the implant.

The term "set time" (or gel time), as used herein, is determined from the initial mixing of components, and refers to the time needed for a mixed and delivered system to set to the point where it can be shaped. This period is characterized by a rapid rise in the slope of the reaction exotherm at the end of the period. By the end of this period, the surface of the gelled biomaterial is preferably tack free and will allow shaping, e.g., by positioning of the condyles. The "cure time", as used herein, is determined from the initial mixing, and refers to the total time needed to mix, shape and fully cure the biomaterial to the desired extent under the conditions used. Preferred polymer systems of this invention preferably provide an induction period that ends within about thirty seconds to two minutes following mixing of the components, followed by a set time of about 3 to about 15 minutes following mixing.

During the curing process (including both setting and completion of cure) the polymer system preferably exhibits an exothem compatible for its intended use, e.g., preferably an exotherm of less than about 70 degrees C to about 90 degrees C, and more preferably less than about 80 degrees C. Given the present description, those skilled in the art will appreciate the manner in which the polymer system can be adjusted in a variety of ways to obtain suitable exotherm, during setting and cure, e.g., by the use of temperature dependent synergistic catalysis. Catalysts suitable for use in compositions of the present invention provide an optimal combination of such properties as set time, cure time, and in turn, viscosity (and flowability) of the curing polymer system.

In a particularly preferred embodiment, the selection of catalyst and other ingredients provides a cure profile that exhibits both synergistic and "delayed action" kinetics, in which induction of cure begins immediately upon mixing the polymer components, and is relatively "flat" during the induction period, without significant increase of viscosity of reaction mixture. This period permits delivery of the "flowable" polymer to the tissue injury site, and is followed by a setting period characterized by variable increase in slope (in a plot of temperature vs. time) that is designed to quickly drive the curing process to completion, and in turn, to quickly provide a set polymer that is sufficiently strong and tack-free to permit final shaping.

The composition of the present invention can be delivered to a site within the body, and there cured, preferably using minimally invasive means, in order to repair (e.g., reconstruct or resurface) tissue such as cartilage, and particularly cartilage associated with diarthroidal and amphiarthroidal joints. Optionally, the composition can be delivered and cured within an implanted mold device. A device as described herein can also be used to deliver biomaterial to a site within the body, e.g., to a mold or a site of damaged or diseased cartilage, to be cured in situ in order to provide an implant or repair the cartilage without undue surgical trauma.

The invention also provides a kit comprising a device as described herein in combination with a plurality of sterile, flowable parts capable of being mixed at the time of use in order to provide a flowable composition and to initiate cure, the parts including: (1) a quasi-prepolymer component comprising the reaction product of one or more polyether polyols, one or more isocyanates, and one or more reactive hydrophobic additives, and (2) a curative component comprising one or more polyether polyols, one or more chain extenders, and one or more catalysts. The device can be used to mixed the quasi-prepolymer component and curative component, in order to deliver the mixture to a tissue site using minimally invasive means.

The biomaterial components can be provided as an integral part of a device of this invention, e.g. prepackaged with the body portion and delivery conduit in order to provide a ready-to-use apparatus. In an alternate embodiment, the device of this invention provides an attachment site for the biomaterial components (e.g., in the form of a receptacle site for component pack or cartridges or an attachment site for component delivery tubes), in combination with a mixing path and delivery conduit. Such a device can be manufactured and sold alone, or in a kit together with the a supply of biomaterial components in a form suitable for attachment and use.

Optionally two or more biomaterial compositions can be delivered, e.g., sequentially, using a device of this invention, for instance to provide a biphasic or a heterogeneous cured material having varying properties. The compositions can each be provided as separate component sources, having flow lines that are separated and common in relevant part. By the operation of one or more additional valves a second composition can be used to displace a first composition, as the second is mixed, with an amount being initially shunted off until it has adequately purged the delivery conduit of the first composition.

Various components of the biomaterial delivery system, including the delivery device itself and biomaterial source can be manufactured, sterilized, and sold alone, or sold together in a kit, e.g., with the biomaterial source being attached or attachable to the device at the time of use. In another alternate embodiment, the invention provides a biomaterial source, per se, for instance in the form of a canister or cartridge pack, adapted to be attached to a device as presently described. The device, biomaterial source, and combined apparatus can be used in a minimally invasive surgical procedure, e.g., for resurfacing a knee, such as that set forth below.

Example of Surgical Application

With a trocar create two arthroscopic portals antermedial and anterolateral. A third optional portal for irrigation of the joint superpatellar may be created. Inspect all compartments of the knee with the arthroscope. If the knee is tight or the medial joint space is narrow during the scope, an external distractor or fixator may be used (e.g., two AO screws and one connecting rod or a Synthes AO femoral distractor). Place one pin just proximal to the origin area of the medial collateral ligament at distal femur and the other pin the area of the distal insertion site of the ligament (proximal medial tibia). If needed a small outside-in capsulotomy/MCL release may be carried out through a small stab wound medially. With the scope in the joint, the surgeon should be able to reach all areas of the medial tibial plateau, including the posterior medial meniscus when the external distractor is deployed and the plateau can be placed horizontal to the floor.

The medial tibial plateau is arthroscopically accessed and prepared so as to remove all of the damaged cartilage on the weight-bearing surface of the medial tibial plateau. The anterior edge of the cavity should be located at the level of the initial upslope of the tibial spine, extend mesial to the base of the tibial spine, lateral and posterior to the edge of the tibial plateau. If necessary, the medial meniscus may be debrided back to a stable rim. No lateral meniscal debridement or chondroplasty in the lateral or patellofemoral compartment should be done. Limited synovectomy in the medial compartment should only be done to improve visualization. Remove any fibrillated cartilage and smooth or feather cobblestone and ridged areas on the medial femoral condyle.

Drill at least three (3) anchoring holes to a depth of 5 mm in the subchondral bone. Create the anchor holes in an inverted cone or gourd-shaped geometry to allow for a mechanical lock of the polymer with the subchondral bone once the polymer solidifies. Flex and extend the knee to flush particles from the posterior pouch, superpatellar fossa and posterior fossa. Suction out all areas of the joint with the arthroscope and dry the implant site.

Remove the components of the biomaterial delivery apparatus, including the delivery unit (including the delivery conduit, disc-like mixing path, and shunt tube or reservoir with valve control), body portion, and pre-heated dual barrel biomaterial cartridge from their packaging and place on the sterile field. Optionally, a conventional straight static mixer can be included and used as well, in a preliminary fashion, to facilitate the removal of any air bubbles that may exist in the biomaterial components.

Remove the tip cap from the cartridge and assemble the straight mixer onto the dual barrel cartridge by means of the twist lock. Place the assembly into the administration gun and slowly remove any bubbles by expressing the initial quasi pre-polymer through the straight mixer in a vertical upwards position, expressing 2–3 ccs of mixed polymer as waste.

After the bubbles are removed, replace the straight mixer with the disc mixer delivery unit. Ensure that the stainless steel sleeve on the cannula part of the disc mixer is extended to form a straight tip. The stainless steel sleeve is now connected with the advancement mechanism of the administration gun.

Introduce the cannula tip through one portal and retract the stainless steel sleeve. The tip of the cannula is now positioned over the lesion site. Practice reaching all anchor holes with deployed tip to ensure access to all holes. Pay attention to the plane of the tibia in order to allow for the polymer to stay level. With a manual drainage assembly, Set the 3-way valve on the disc mixer such as to discard the mixed polymer through the drainage tubing. Express 3–5 ccs of mixed polymer through drain tubing and stop. Using a plunger-cylinder assembly, a predetermined amount of biomaterial will fill the cylinder, moving the plunger up and opening a direct flow path from the mixing elements to the delivery tip. After manually or automatically shunting biomaterial, begin straight passage of the mixed polymer through the cannula and express the polymer into each of the anchor holes and over the prepared subchondral bone to completely fill the lesion site. While maintaining arthroscopic vision, remove all other instruments from the implant site and allow the material to polymerize to a semi-solid non-tacky state. Withdraw the arthroscope and close the portals (if desired). Keep leg flexed to 90° for 30 minutes post implant (using functional implant and perform a second polymer application. At 30 minutes, extend the leg to zero (0°) degrees in brace. Keep the leg in the extended position for 24 hours.

The patient can be discharged the same day, non weight-bearing locked in extension in brace, and can resume fall weight-bearing in 24 hours with brace removed. The patient is recommended to be treated by a physical therapist with range of motion and strengthening exercises for approximately 8 weeks.

The present invention has been described with respect various preferred embodiments, which, together with other conditions and details should not be construed to unduly limit this invention.

What is claimed is:

1. A device for mixing and delivering a curable biomaterial, the device comprising:
   (a) an attachment site for a biomaterial source, the source comprising a plurality of biomaterial components adapted to be mixed in order to initiate cure,
   (b) a body portion comprising
      i) a handle for gripping and actuating the device, and
      ii) a biomaterial mixing path having inlet and exit ends, the inlet end of the mixing path adapted to be placed in fluid communication with the biomaterial component source, the mixing path being adapted to combine and mix the components within a time suitable to permit the mixed components to traverse the mixing path in a flowable fashion, and within an longitudinal distance adapted to provide controllable, ergonomic operation in the course of minimally invasive surgery, and
   (c) a delivery unit comprising a deliver conduit having an inlet end in fluid communication with the exit end of the mixing path, and an exit end adapted to deliver the mixed biomaterial to a tissue site,
   wherein the device is adapted for single-handed operation, and the mixing path provides a longitudinal length dimension to the device that is on the order of one-tenth, or less, the overall length of the mixing path, and
   further comprising a mechanism for controllably shunting an initial portion of mixed biomaterial.

2. A device according to claim 1 wherein the mechanism comprises a plunger and a cylinder assembly disposed in fluid communication between the outlet end of the mixing path and the inlet end of the delivery conduit adapted to permit a predetermined volume of biomaterial to enter the cylinder, and raise the plunger in a manner that redirects the flow of biomaterial to the conduit upon shunting a predetermined volume of biomaterial.

3. A device for mixing and delivering a curable biomaterial, the device comprising:
   (a) an attachment site for a biomaterial source, the source comprising a plurality of biomaterial components adapted to be mixed in order to initiate cure,
   (b) a body portion comprising
      i) a handle for gripping and actuating the device, and
      ii) a biomaterial mixing path having inlet and exit ends, the inlet end of the mixing path adapted to be placed in fluid communication with the biomaterial component source, the mixing path being adapted to combine and mix the components within a time suitable to permit the mixed components to traverse the mixing path in a flowable fashion, and within an longitudinal distance adapted to provide controllable, ergonomic operation in the course of minimally invasive surgery, and (c) a delivery unit comprising a deliver conduit having an inlet end in fluid communication with the exit end of the mixing path, and an exit end adapted to deliver the mixed biomaterial to a tissue site, wherein the device is adapted for single-handed operation, and the mixing path provides a longitudinal length dimension to the device that is on the order of one-tenth, or less, the overall length of the mixing path, and further comprising a retractable sheath covering the delivery conduit and an operable control associated with the handle portion.

4. A device for mixing and delivering a curable biomaterial, the device comprising:

(a) an attachment site for a biomaterial source, the source comprising a plurality of biomaterial components adapted to be mixed in order to initiate cure, (b) a body portion comprising
   i) a handle for gripping and actuating the device, and
   ii) a biomaterial mixing path having inlet and exit ends, the inlet end of the mixing path adapted to be placed in fluid communication with the biomaterial component source, the mixing path being adapted to combine and mix the components within a time suitable to permit the mixed components to traverse the mixing path in a flowable fashion, and within an longitudinal distance adapted to provide controllable, ergonomic operation in the course of minimally invasive surgery, and (c) a delivery unit comprising a delivery conduit having an inlet end in fluid communication with the exit end of the mixing path, and an exit end adapted to deliver the mixed biomaterial to a tissue site, wherein the device is adapted for single-handed operation, and the device further comprises a mechanism for controllably shunting an initial portion of mixed biomaterial.

5. A device according to claim 4 wherein the mechanism comprises a plunger and cylinder assembly disposed in fluid communication between the outlet end of the mixing path and the inlet end of the delivery conduit and adapted to permit a predetermined volume of biomaterial to enter the cylinder, and raise the plunger in a manner that redirects the flow of biomaterial to the conduit upon shunting a predetermined volume of biomaterial.

6. A device according to claim 5 wherein the mixing path provides a longitudinal length dimension to the device that is on the order of one-tenth, or less, the overall length of the mixing path, the mixing path contains between about 30 and about 40 elements within a mixing flow path of between about 20 cm and about 30 cm, and the biomaterial source comprises a two part polyurethane system provided in the form of a syringe cartridge pack.

7. A device according to claim 4 further comprising a retractable sheath covering the delivery conduit and an operable control associated with the handle portion.

8. A device according to claim 4 wherein the mixing path contains between about 10 and about 100 elements within a mixing flow path of between about 10 cm and about 50 cm, the mixing flow path contributing between about 1 cm and about 5 cm to the longitudinal dimension of the device.

9. A device according to claim 8 wherein the mixing path contains between about 30 and about 40 elements within a mixing flow path of between about 20 cm and about 30 cm.

10. A device according to claim 4 wherein the biomaterial source comprises a two part polyurethane system.

11. A device according to claim 10 wherein the components are adapted to be mixed at a ratio of 1 to 1 by volume.

12. A device according to claim 4 wherein the biomaterial source is provided in the form of a syringe cartridge pack.

13. A device according to claim 12 wherein the biomaterial comprises a polyurethane.

14. A device for mixing and delivering a curable biomaterial, the device comprising:

(a) an attachment site for a biomaterial source, the source comprising a plurality of biomaterial components adapted to be mixed in order to initiate cure, (b) a body portion comprising
   i) a handle for gripping and actuating the device, and
   ii) a biomaterial mixing path having inlet and exit ends, the inlet end of the mixing path adapted to be placed in fluid communication with the biomaterial component source, the mixing path being adapted to combine and mix the components within a time suitable to permit the mixed components to traverse the mixing path in a flowable fashion, and within an longitudinal distance adapted to provide controllable, ergonomic operation in the course of minimally invasive surgery, and (c) a delivery unit comprising a delivery conduit having an inlet end in fluid communication with the exit end of the mixing path, and an exit end adapted to deliver the mixed biomaterial to a tissue site, wherein the device further comprises a retractable sheath covering the delivery conduit and an operable control associated with the handle portion.

15. A device according to claim 14 wherein the mixing path contains between about 10 and about 100 elements within a mixing flow path of between about 10 cm and about 50 cm, the mixing flow path contributing between about 1 cm and about 5 cm to the longitudinal dimension of the device.

16. A device according to claim 14 wherein the mixing path contains between about 30 and about 40 elements within a mixing flow path of between about 20 cm and about 30 cm.

17. A device according to claim 14 wherein the biomaterial source comprises a two part polyurethane system.

18. A device according to claim 17 wherein the components are adapted to be mixed at a ratio of 1 to 1 by volume.

19. A device according to claim 14 wherein the biomaterial source is provided in the form of a syringe cartridge pack.

* * * * *